US005483821A

United States Patent [19]
Mazzoleni et al.

[11] Patent Number: 5,483,821
[45] Date of Patent: * Jan. 16, 1996

[54] BRINELL HARDNESS-MEASURING PROBE WITH CENTERING DEVICE

[75] Inventors: Giancarlo Mazzoleni, Horsham; Gordon M. Baker, Doylestown, both of Pa.

[73] Assignee: Newage Industries, Willow Grove, Pa.

[*] Notice: The portion of the term of this patent subsequent to Sep. 29, 2009, has been disclaimed.

[21] Appl. No.: 106,028

[22] Filed: Aug. 13, 1993

Related U.S. Application Data

[63] Continuation-in-part of Ser. No. 657,596, filed as PCT/US92/01258, Feb. 18, 1992, Pat. No. 5,150,608.

[51] Int. Cl.$^6$ .................................................. G01N 3/48
[52] U.S. Cl. ............................................................ 73/82
[58] Field of Search ..................... 73/81–83; 356/379, 356/384

[56] References Cited

U.S. PATENT DOCUMENTS

| D. 283,599 | 4/1986 | Biddle, Jr. et al. | D10/46 |
| D. 304,427 | 11/1989 | Biddle | D10/83 |
| 2,305,760 | 12/1942 | Bernhardt | 73/81 |
| 3,370,356 | 2/1968 | Jend | 33/169 |

(List continued on next page.)

FOREIGN PATENT DOCUMENTS

| 0367299 | 5/1990 | European Pat. Off. . |
| 0620104 | 11/1935 | Germany . |

(List continued on next page.)

OTHER PUBLICATIONS

Patent Abstracts of Japan, vol. 9, No. 232 (P–389) 1955, 18 Sep. 1985 reporting on JP–60 88 350 (Shimazu), published May 18, 1985 (English language Abstract only).

European Search Report for EP 92 90 7169 (2 pages).
Annex to European Search Report for EP 92 90 7169 (2 pages).
NewAge Industries Testing Instrument Division *Technical Bulletin*. "A Major Development in Brinell Hardness Testing from NewAge Industries. The B.O.S.S.", 1 sheet (two–sided).
NewAge Industries Inc. brochure. "NewAge Brinell Scopes Improves Accuracy & Speed of Brinell Impression Measurement", 1 sheet (two–sided).
*Engineering (incl. Machine Shop Magazine)*, vol. 217, No. 5, May 1977, London, Great Britain, p. 413.

*Primary Examiner*—R. Raevis
*Attorney, Agent, or Firm*—Panitch Schwarze Jacobs & Nadel

[57] ABSTRACT

Centering devices are provided for use with Brinell hardness measuring instruments, particularly electro-optical probes, which include one or more illumination sources in a housing having an aperture at one end which is aligned with an optical axis of the probe to provide the optics a view of the specimen surface opposite the opening. In one embodiment, a spider-like centering structure is provided protruding through the probe end opening. The centering structure directs light from source in the probe directly into an indentation in a specimen surface engaging the centering structure and prevents light from crossing the indentation and reducing edge contrast. A mask further prevents spillage of light from each source onto the specimen surface adjoining the indentation and the source so as to heighten contrast differences between the bright surface of the indentation and the dark surrounding specimen surface. Diametric measurements and hardness determinations can be performed without visual observation of the illuminated indentation by an operator. Specimen hardness can be determined from illumination intensity data generated and gathered during a single illumination of the indentation taking about 1/30th of a second. Another device includes a source developing a beam of visible light, which is directed through the probe end opening with sufficient intensity to permit an operator to locate and at least generally align the probe end with an indentation using the light beam.

21 Claims, 6 Drawing Sheets

| | | | |
|---|---|---|---|
| 3,754,436 | 8/1973 | Saxton | 73/81 |
| 3,763,697 | 10/1973 | Sturm | 73/81 |
| 4,147,052 | 4/1979 | Tsujiuchi et al. | 73/81 |
| 4,277,174 | 7/1981 | Kleesattel | 356/372 |
| 4,627,096 | 12/1986 | Grattoni et al. | 382/8 |
| 4,945,490 | 7/1990 | Biddle, Jr.; et al. | 364/506 |
| 5,150,608 | 9/1992 | Mazzoleni et al. | 73/81 |

FOREIGN PATENT DOCUMENTS

| | | | |
|---|---|---|---|
| 2445966 | 4/1976 | Germany . | |
| 0042838 | 3/1982 | Japan | 73/81 |
| 0467806 | 6/1937 | United Kingdom | 73/81 |
| 1223181 | 2/1971 | United Kingdom . | |

BRINELL HARDNESS-MEASURING PROBE WITH CENTERING DEVICE

RELATED APPLICATION

This is a continuation-in-part of U.S. patent application Ser. No. 07/657,596 filed Feb. 19, 1991, now U.S. Pat. No. 5,150,608, and of International Application Serial No. PCT/US92/01258 filed Feb. 18, 1992, which are incorporated by reference.

FIELD OF THE INVENTION

The invention relates generally to hardness testing and specifically to methods and apparatus for determination of Brinell indentation diameters for hardness testing.

BACKGROUND OF THE INVENTION

Hardness of metal may be determined by indenting a metal specimen at a known force using a known device and measuring either the depth or diameter of the indentation. Diametric testing is most commonly referred to as Brinell testing, and is described in ASTM E10 (10-78), incorporated herein by reference.

In Brinell testing, a ball penetrator, either 5 mm or, more typically, 10 mm in diameter, is applied to a test specimen surface with a predetermined load to produce a generally spherical indentation in the specimen surface. Knowing the applied force, the Brinell hardness of the test specimen can be determined from the diameter of the indentation.

Current Brinell testing involves measuring the diameter of the indentation along orthogonal axes using either a small optical microscope with a graded reticle or, more recently, an electro-optical instrument with a probe which indicates or responds to, respectively, the differences in light reflected from the specimen surrounding the indentation, the raised side walls adjoining the indentation and the indentation itself. Each type of instrument can be positioned over and against a specimen. Each instrument generates an image of the underlying specimen surface. The operator moves the instrument to try to center the instrument over the center of the indentation. Each instrument also typically employs light focused or otherwise directed through at least part of the instrument so that when the central axis of the scope or probe is perpendicular to the specimen surface, the light also strikes the specimen surface beneath the instrument to illuminate that area including the indentation.

A major problem with each type of apparatus is the difficulty in locating and then accurately centering the instrument with respect to the indentation. In most instances, a field of view relatively large with respect to the size of the indentation must be provided in order to permit the operator to view a sufficiently large area of the specimen surface to orient the probe with respect to the indentation. In some instances, due to a roughness of the specimen surface and/or the polish of the side walls of the indentation, the contrast between light reflected from the undisturbed surface and the indentation is relatively low, making it difficult for the operator to optically identify the indentation and the center of the indentation. While the newest Brinell hardness-measuring electro-optical probes are configured to compensate for misalignment of the probe with respect to the central axis of the indentation, such misalignment between the indentation and the central optical axis of the probe can still lead to some degradation of accuracy in the diameter measurement, particularly if the probe is significantly off center.

Because a relatively large field of view is typically provided to the optical system to permit the operator to find the indentation, the resolution of the optical system is further reduced.

Another problem arises with the electro-optical probes in connection with the miniaturization of such systems for portability. Stationary systems can provide a CRT to image the specimen surface for the operator. Existing portable systems use liquid crystal displays to depict the specimen's surface and impression for the operator. The processing capability required to generate and maintain these specimen surface reproduction displays are typically a significant portion to total processing capability of the portable unit. Consequently, such units take undesirably long periods of time to perform measurements and provide a determination of Brinell hardness.

It would be desirable to provide a means and a method to simplify alignment of a Brinell hardness optical measuring apparatus, particularly one having an electro-optical probe, with a Brinell indentation which does not adversely affect the measurement results.

It also would be desirable to provide the means and method to simplify portable Brinell hardness measuring apparatus with electro-optical probes which dispense with the need to generate a display duplicating the specimen surface for the operator in order to align the probe with the Brinell impression for accurate Brinell hardness determination.

SUMMARY OF THE INVENTION

In one aspect the invention is an improvement in an electro-optical apparatus for determining hardness of a specimen by diametric measurement of an indentation in a surface of the specimen, the apparatus including a probe and an electronic processor coupled with the probe, the probe including an opening at one end thereof, the probe further including an artificial illumination source located to illuminate a specimen surface through the opening and optics within the probe located to view the specimen surface exposed through the opening as illuminated by the illumination source. The improvement comprises a separate centering device having an alignment guide projecting outwardly from the probe through the opening. The alignment guide enters an indentation when the indentation is at least generally aligned with the opening.

In another aspect, the invention is an improvement in an apparatus for determining hardness of a specimen by diametric measurement of an indentation in a surface of the specimen, the apparatus including an instrument with an opening at one end thereof, and optics within the instrument configured for viewing the specimen surface exposed through the opening. The improvement comprises a centering device including an alignment guide projecting through the opening, the alignment guide entering an indentation when the indentation is at least generally aligned with the opening and the alignment guide.

In another aspect, the invention is an improved Brinell hardness-determining apparatus comprising: an instrument having an end configured for placement on a specimen surface to be examined and an opening through the end providing a field of view within the instrument of the specimen surface on which the end of the instrument is placed; an alignment member having a central axis and two opposing axial sides, a central portion of the alignment member, being aligned generally with respect to the central axis and protruding from one axial side of the alignment member through the opening aligned to define a centering structure, the centering structure being shaped to mate with an indentation of generally predetermined shape in the specimen surface. The central portion of the alignment member is further configured to freely pass light axially through the alignment member, generally around the central axis, whereby the field of view of the instrument through the opening is at least substantially unblocked. The central portion of the alignment member further has a generally light distributing surface finish. At least one light source is located proximal the one end of the instrument and is positioned to bounce light off the central portion of the alignment member and into the indentation mated with the alignment member so as to illuminate the circular indentation to a greater degree than the light source illuminates the specimen surface adjoining the indentation.

In yet another aspect, the invention is an improvement for hardness determination using diametric measurements of an at least generally circular indentation and a specimen surface comprising the steps of: illuminating the indentation to a greater degree than the specimen surface is illuminated immediately adjoining the indentation and thereby establishing a contrast between brighter portions of the indentation immediately adjoining a circumferential edge of the indentation and darker portions of the specimen surface immediately adjoining the circumferential edge and the brighter portions of the indentation at least essentially entirely around the indentation; and sensing illumination intensity from the indentation and the specimen surface immediately adjoining the circumferential edge of the indentation at least essentially entirely around the indentation from directly opposite the indentation during the illuminating step.

In yet another aspect, the invention is an improvement for hardness determination using diametric measurements of an at least generally circular indentation in a specimen surface comprising the steps of: illuminating the indentation to a greater degree than the specimen's surface is illuminated proximal to the indentation and thereby establish a contrast between brighter portions of the indentation and darker portions of the specimen's surface immediately adjoining the brighter portions of the indentation, at least essentially entirely around the indentation.

In yet another aspect, the invention is a probe for an electo-optical apparatus for determining hardness of a specimen by diametric measurement of an indentation in a surface of the specimen. The probe comprises a housing with an opening at one end thereof; an artificial illumination source located within the probe housing so as to illuminate a specimen surface through the opening; optics located within the probe housing so as to view the specimen surface exposed through the opening as illuminated by the artificial illumination source; and a light guiding device mounted on the probe between at least one artificial illumination source of the probe and the one end of the probe. The light guiding device is positioned and configured to direct light from the at least one artificial illumination source into only a portion of an indentation aligned against the one opening and to simultaneously prevent light from the at least one artificial illumination source from entering a remaining portion of the aligned indentation.

BRIEF DESCRIPTION OF THE DRAWINGS

The foregoing summary as well as the following detailed description of the presently preferred embodiment of the invention will be better understood when read in conjunction with the appended drawings. For the purpose of illustrating the invention, there is shown in the drawings an embodiment which is presently preferred. It should be understood, however, that the present invention is not limited to the particular arrangements and instrumentalities shown. In the drawings.

DETAILED DESCRIPTION OF PREFERRED EMBODIMENT

Like reference numerals are used to identify the same elements in the various drawings.

Figure 1:
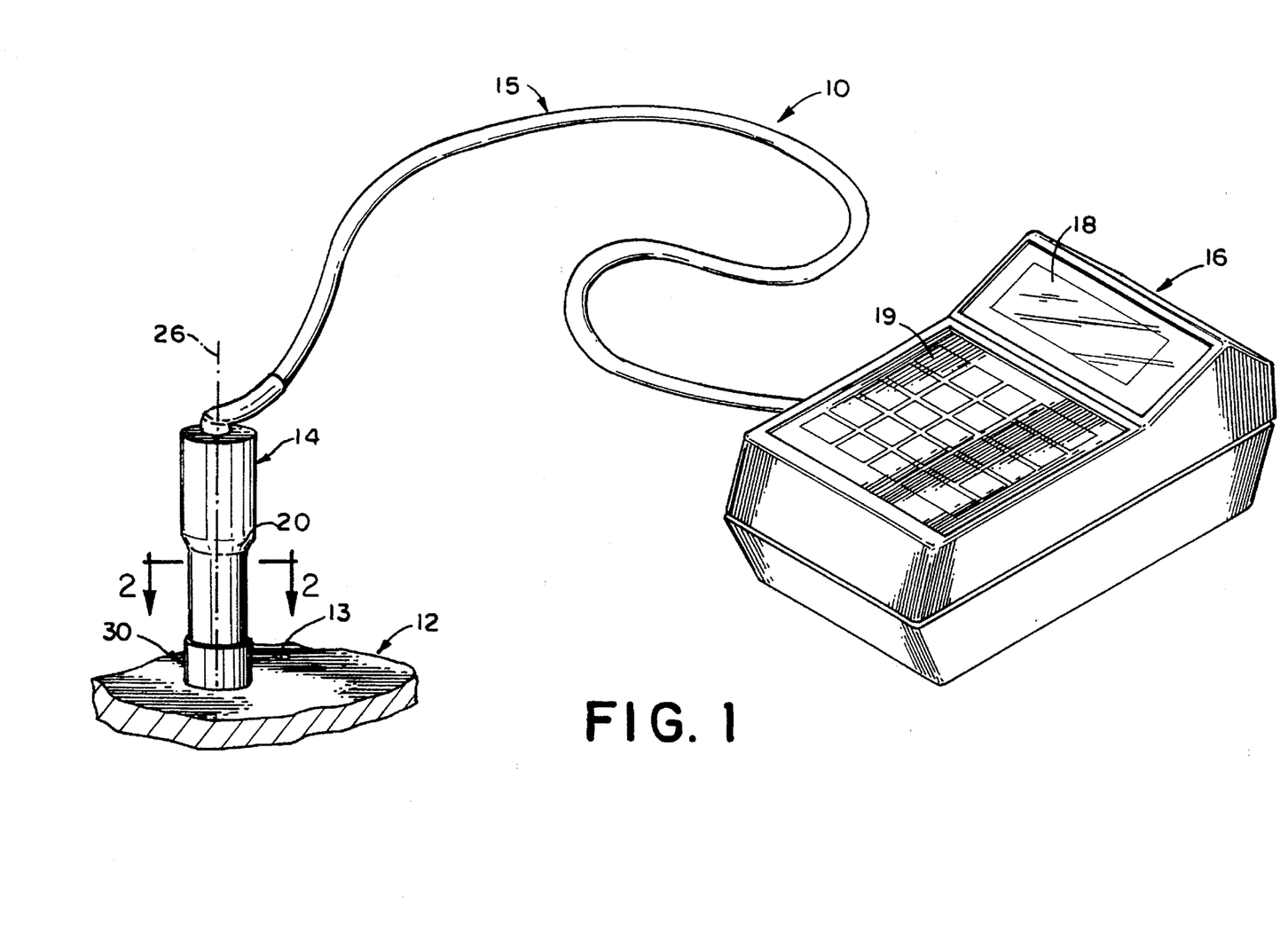
FIG. 1 depicts a portable Brinell hardness-measuring apparatus including a hand-held electro-optical probe-type instrument mounting a first embodiment centering device of the present invention.

FIG. 1 depicts schematically an exemplary, electro-optically configured Brinell hardness-measuring apparatus indicated generally at 10 and, in conjunction with it, a specimen 12 the hardness of which is being measured. Electro-optical Brinell hardness measuring apparatus are known and have been disclosed and discussed in a variety of U.S. patents, including, for example, U.S. Pat. No. 4,945,490, which is incorporated by reference herein in its entirety, as well as in other printed, published literature. The novelty of the present invention resides in centering devices to be described which are improvements to such instruments as well as to manual, microscope type Brinell hardness-measuring instruments, either as an aftermarket accessory or, preferably, configured into the instruments during original manufacture.

The exemplary Brinell measuring apparatus 10 in FIG. 1 includes a hand-held, electro-optical instrument or probe 14, physically and electrically coupled by appropriate flexible cabling 15 with an associated electronic processor 16 preferably including an optical display 18 and keyboard 19. The probe 14 includes an outer, generally tubular housing 20 which typically contains at least one and preferably a plurality of internal artificial illumination light sources 23 indicated diagrammatically in FIG. 3. The probe housing further includes a photoresponsive subsystem typically with at least some optics which are indicated diagrammatically at 22a, and some type of photoresponsive element, which is indicated diagrammatically at 22b. Optics 22a is typically a lens or lens system which focuses an image of opening 25 on element 22b. The probe 14 has one end 24 with a preferably circular (see FIG. 2) opening 25 therethrough, preferably centrally located with respect to the housing 20 and end 24. The end 24 is preferably planar for butting the end against a planar surface of a specimen. Other shapes could be provided to conform to other specimen surface configurations.

Light source 23 and the photoresponsive subsystem 22a/22b respectively illuminate and receive light reflected from the surface of a specimen 12 positioned at the opening 25. Power is typically supplied to light source 23 in the probe 14 through the cabling 15 from the processor 16. The photoresponsive subsystem 22a/22b typically generates one or more electrical signals in response to light reflected on the subsystem, particularly the optics in the probe 14. The signal or signals are returned from the probe 14 to the processor 16 through the cabling 15 for processing. While the photoresponsive subsystem typically includes a CCD array or other transducer(s) 22b, the photoresponsive subsystem in the probe may be passive, with element 22b being an optical wave guide or bundle of guides suitable to carry an image back to the processor 16 where a photoelectric array may be located to respond to the image. The probe optics 22a focus an appropriate image on the active or passive component of the subsystem used to pass information back to the processor.

The opening 25 provides a field of view to the illumination light source 23 and to the optics 22 of the photoresponsive subsystem of the probe 14 of the surface of the specimen 12 against which the end 24 of the probe 14 is placed. Preferably the optic elements of the probe 14 have a central optical axis which, in the case of the probe 14 of the present example, is preferably coincident with the central axis of the outer tubular housing 20 and center axis of opening 25. This central, coincident axis is indicated diagrammatically at 26 in the figures.

Figure 2:
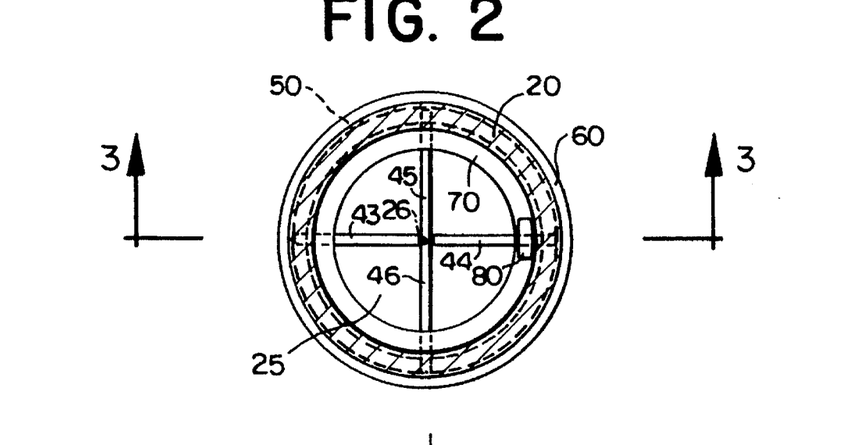
FIG. 2 is a diagrammatic cross-sectional view of the probe taken along the lines 2—2 of FIG. 1.
Figure 3:
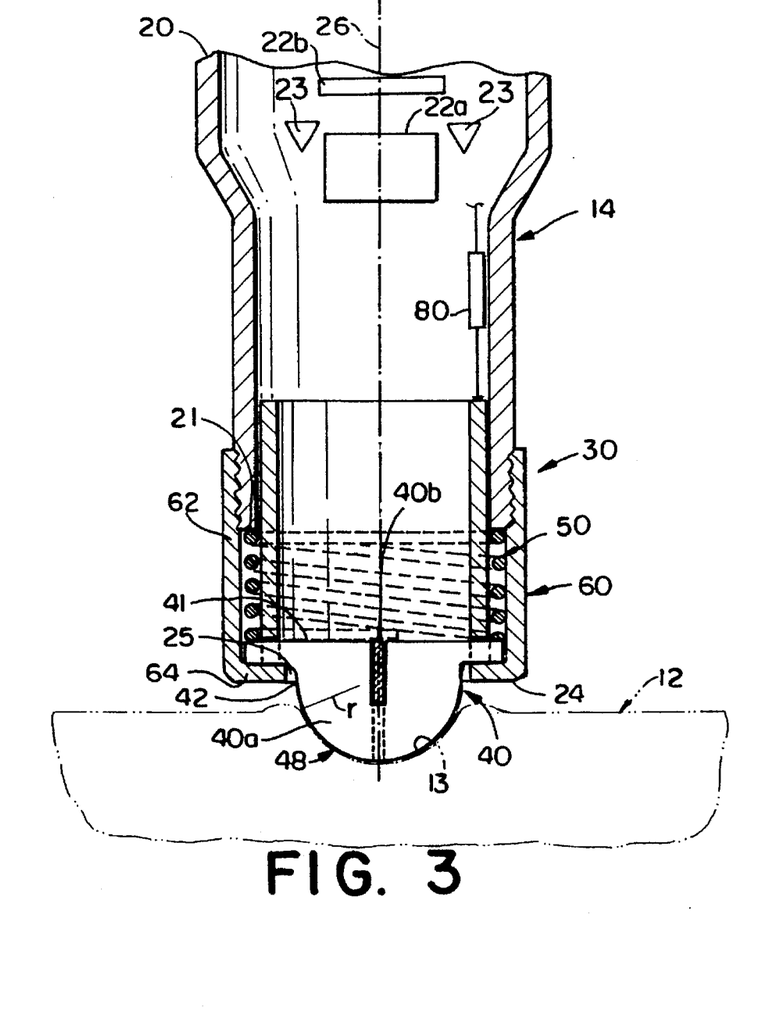
FIG. 3 is a cross-sectional view of the probe taken along the lines 3—3 of FIG. 2.

Mounted at the one working end 24 of the probe 14 is a first embodiment, mechanical type centering device of the present invention, which is indicated generally at 30 in the figures. Referring to FIGS. 2 and 3, the basic centering device 30 preferably comprises an alignment member, indicated generally at 40, and biasing means, indicated generally at 50.

Referring specifically to FIG. 3, the preferred alignment member 40 has a central axis which is at least generally coincident with the central axis 26 of the probe 14. The alignment member 40 has two axial sides, indicated generally at 41 and 42. The alignment member 40 is preferably formed by two interfitted pieces 40a, 40b defining four arms 43, 44, 45 and 46 extending radially with respect to the central axis of the centering device, as represented by the coincident central axis 26 in the figures. Each of the pieces 40a, 40b and each of the arms 43–46 is perpendicular to its adjoining neighbor. This is best seen in FIG. 2. The portion of each arm 43–46 adjoining central axis 26 extends radially away from the axis 26 with a radius of curvature "r" forming a convexly curved, quarter round outer surface. After curving through an arc of approximately 90°, each arm 43–46 thereafter extends radially outwardly from the central axis 26 in a direction generally perpendicular to said axis 26. Collectively, the radiused portions of the arms 43–46 define centering structure 48, protruding generally concentrically with respect to the central axis 26 on one axial side 42 of the alignment member 40 through the opening 25, which acts as a mechanical instrument alignment guide. As is indicated in FIG. 2, the arms 43–46 leave open a major proportion of the central area of the alignment guide, which is the portion of alignment member 40 circumscribed by the opening 25 in end 24 of the probe 14. This open central area permits Light to pass freely between the optical component(s) within the probe and the opposing specimen 12, whereby the field of view of the optics 22 of the probe 14 through opening 25 is at least substantially unblocked, permitting the probe 14 to make/take optical readings axially through the alignment guide 40.

The alignment member 40 is biased away from the proximal end 24 of the probe housing. Preferably the biasing is provided by a coil spring also identified by the same reference number 50, or one or more other suitable biasing member(s). Preferably, the alignment member 40 and biasing spring 50 are held concentrically with respect to one another and the central axis 26 by a the coupling indicated at 60, which is preferably provided in the described embodiment by a generally tubular collar member, indicated by the same reference number 60. The collar 60 may be an original portion of the housing of a new probe or an adaptor for replacement of an end portion of an existing probe housing. Coupling collar 60 preferably includes a generally cylindrical wall 62, concentric with the central axis 26, preferably threaded on an inner circumferential side at one end to engage threading which has been provided on an adjoining tubular portion of housing 20 of the probe 14. An annular flange 64 extends radially inwardly from the cylindrical wall 62, at the end of the wall spaced farthest from the remainder of the probe 14, and defines the surface of the one end 24 of the probe and the opening 25 therethrough. The flange 64 retains the alignment member 40 and biasing means spring 50 within the probe 14. In this way, the coupling collar 60 couples the alignment member 40 and biasing spring 50 with the remainder of the probe 14 such that the central axis of the alignment member 40 is generally coincident with the central axis 26 of the probe and opening 25 and such that the alignment member 40 is supported for movement in the axial direction with respect to the probe 14, biased away from the remainder of the probe 14 by the biasing spring 50.

The alignment member 40 may be formed, for example, by at least one and preferably a pair of planar, stamped metal pieces. The pair are slotted and interfitted perpendicularly at their centers to form the four radiating arms 43–46. It is envisioned each arm might be approximately fifteen mils thick and at least about one hundred twenty-five mils high with a radius of curvature "r" of 5 mm to mate with a circular indentation 13 in the surface of specimen 12 formed by a 10 mm diameter Brinell ball penetrator. Where a ball penetrator of a different diameter is employed, the radii of the curvature of arms 43–46 are adjusted accordingly.

Preferably, the centering device 30 further comprises a ring member 70 sized for slidable movement within the adjoining outer tubular portion of housing 20 of the probe 14. Ring member 70 assists in keeping the biasing means spring 50 in concentric position and in keeping the alignment member 40 from pitching severely, causing it to possibly dislodge from the probe 14 or jam within the probe 14. Preferably, too, the alignment member 40 is coupled with the ring member 70 in a way which retards relative movement between the alignment member 40 and the ring in member 70, such as, for example, by the provision of slots at the lower end of the ring member 70 which receive each of the arms 43–46. Preferably, the arms 43–46 of the alignment member 40 are fixedly secured with the ring member 70 by soldering, spot welding, adhesive, frictional engagement or other means suitable for the materials selected to form an integral structure, which itself constitutes an alternate embodiment alignment member of the present invention.

It is further contemplated that the centering device 30 of the present invention will include a switch, indicated diagrammatically at 80, which is configured and located to respond to the depression of the probe 14 against the specimen 12 after receipt of the centering structure 48 in a Brinell penetrator indentation, such as indentation 13 illustrated in FIG. 3. The switch 80 will be discussed further with respect to the following discussion of the operation of the centering device 30 with the probe 14.

The optical, working end 24 of the probe 14 with the centering device 30 is positioned by the operator against the surface of specimen 12 bearing one or more of the Brinell indentations 13. The operator moves the probe 14 across the surface of the specimen 12 with the centering structure alignment guide 48 contacting and running across the surface, visually aligning the probe with an indentation until the protruding centering structure 48 is caught in the indentation 13. Once the centering structure enters the indentation 13, the annular flange portion 64 of the coupling member 60 at end face 24 is pressed against the facing surface of the specimen 12 to automatically center and vertically align and space the probe 14 with respect to that surface. In this way, the probe 14 can be virtually automatically aligned with respect to the indentation 13 in a manner which eliminates the incremental movement required of prior instruments without the present centering device. It also eliminates the need to generate a specimen surface display for the operator, thereby greatly reducing the computation load on the processor 16 and greatly increasing the response time of the portable instrument 10.

Preferably, the switch 80 is one that will respond to the upward movement of the alignment member 40, for example, a switch responsive to the movement of the ring member 70 or alignment member 40 away from a position occupied by either of those members before alignment is achieved and the probe depressed against the specimen surface. Such a switch can include, for example, but is not limited to a throw switch, a momentary contact switch, a Hall effect or other proximity switch, a photoresponsive element exposed (or covered) by movement of the ring member 70, a pressure biasing means spring 50, a contact switch formed by overlapping contacting conductive portions of the ring 70 and housing 20 or alignment member 40 and coupling means/member 60 or any number of other possible switching means, any of which could be selected and incorporated into the centering device 30 (and/or the probe 14) in any of a variety of ways. The processor 16 of the instrument 10 can be configured to respond to such a signal to begin a series of automatic measurements and computations leading to the derivation of a Brinell hardness value assigned to the specimen 12 as a result of automatic diametral measurements of the indentation 13.

It is further believed that the alignment member 40 can assist the apparatus 10 in its diametric measurement by improving distribution of the illumination source lighting within the impression. At least one and preferably plural illumination light sources, for example a plurality of individual LED's, are located in or on the probe housing 20 spaced radially from the optical axis 26 and preferably uniformly angularly spaced around that axis, pitched at an angle to that axis, for example about 45°, so as to direct illumination light through the aperture 25 and an open center of the alignment guide centering structure 48 into the impression 13 at an angle to the central axis 26 so as to strike the various sides of the alignment member 40 which in turn reflect and disperse the light within the impression 13. By illuminating the interior of the impression 13 in this fashion, a greater contrast can be obtained between the impression 13 and the adjoining exposed surface of the sample 12 as centering structure 48 further prevents light from completely crossing the indentation 13.

Centering devices of the present invention can equally be incorporated into manual, microscope-type Brinell hardness-determining instruments. The centering device 30, for example, would again be incorporated into the optical working end of the scope, either during original design and manufacture of the scope or, in at least some cases, by being retrofitted into a conventional instrument. Scope-type instruments are typically provided with a reticle having a single diametral axis which is gradiated numerically from the left to right. Typically, the operator attempts to align the reticle with the Brinell penetrator indentation in a way in which the operator can read off the diameters of the indentation. This typically requires considerable incremental movement of the scope to properly position the reticle with respect to the indentation.

Figure 4:
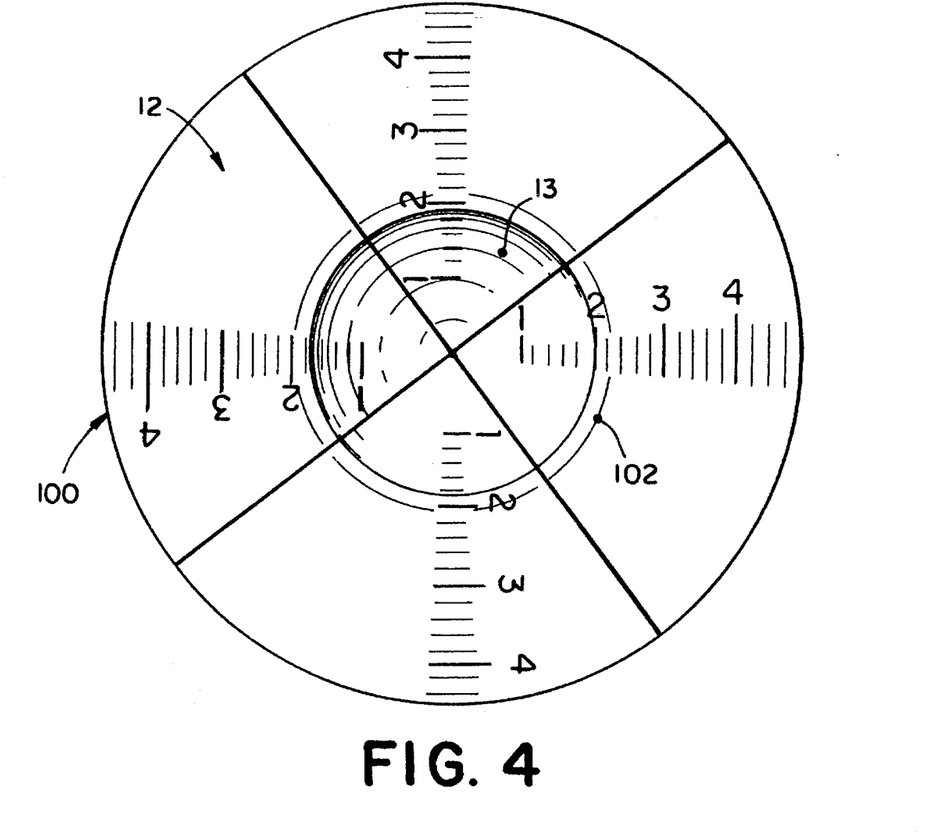
FIG. 4 depicts diagrammatically a preferred reticle used with a Brinell hardness-determining microscope equipped with the centering device of the present invention.

The centering device of the present invention greatly simplifies not only the alignment process but the subsequent measurement process of such scopes. Since the centering structure of the centering device of the present invention aligns the optical axis of the scope with the center of the indentation receiving the centering structure 48, a cross-hair type reticle like reticle 100 in FIG. 4 can be provided inscribed with diametral as opposed to radial values along each radial arm ("1", "2", "3", "4" mm, etc.) of the cross hair so that the operator can tell, at a glance, by simply reading the numbers from the gradiated scale, the diameter(s) of the indentation regardless of the rotational position of the scope. In addition, because the centering device of the present invention accurately aligns a scope on which it is installed concentrically with an indentation to be measured, it permits the possibility of providing GO/NO-GO type reticles for product grading. Such a reticle would be scored or otherwise marked in some way, for example, to provide a circle like circle 102, or segments of such a circle, to indicate a maximum indentation diameter corresponding to a minimum specified hardness. Thus, in FIG. 4 indentation 13 lies within circle 102 indicating the sample is sufficiently hard. Where a hardness range is to be verified, a pair of GO/NO-GO circles or the like could be provided, one to indicate a minimum diameter permitted by a maximum hardness tolerance for a specific material and a maximum diameter marking for a minimum hardness tolerance permitted for the material by the specification. The operator would simply verify that the rim of the indentation 13 lies within the two sets of marking to assure that the sample lies within the specified hardness tolerance range. In addition, many Brinell hardness-testing scopes are provided with removable eye pieces which contain the reticle. Thus, such instrument could easily be modified to measure different hardnesses or to measure indentation diameter to determine a hardness simply by substituting a different eye piece. In addition, in those existing scopes in which it would be difficult to retrofit a centering device of the present invention without altering the spacing of the original working end of the scope from its optics, it would be possible to add a centering device to the existing working end of such a scope and provide a new eye piece, the optics of which are altered to take into account the increased spacing provided between the optics from the addition of the centering device to the working end of the scope.

Figures 5, 6:
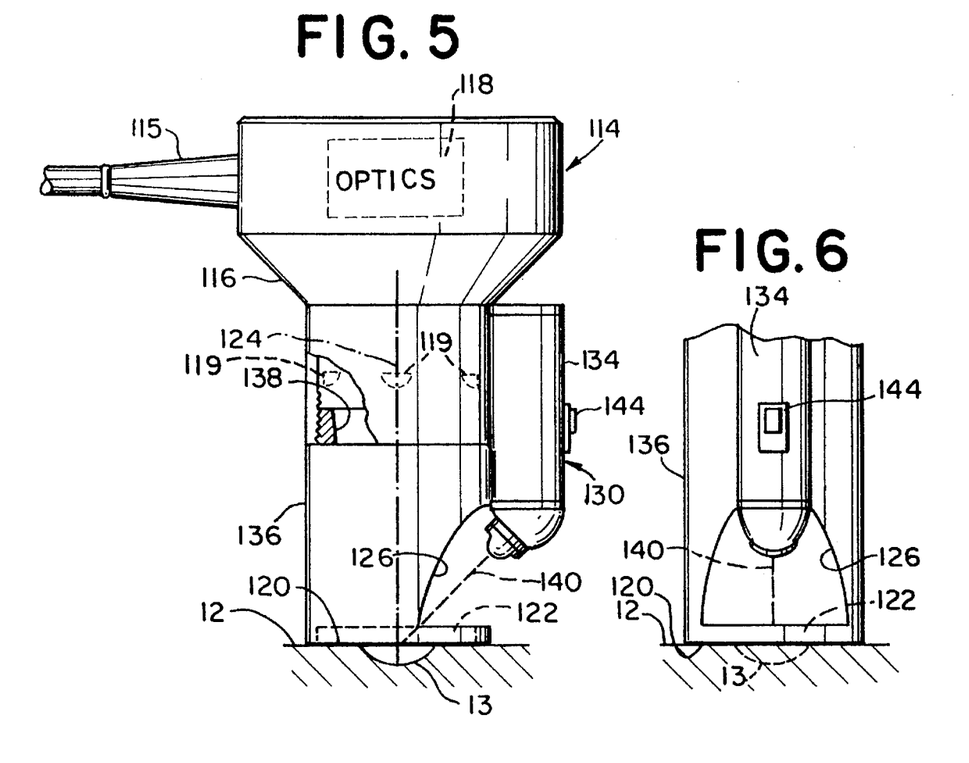
FIG. 5 is a partially broken away, diagrammatic side elevation of a probe of a portable electro-optical Brinell hardness-determining instrument including a second embodiment centering device of the present invention.
FIG. 6 is a localized side elevation of the second embodiment device of FIG. 5.
Figure 7:
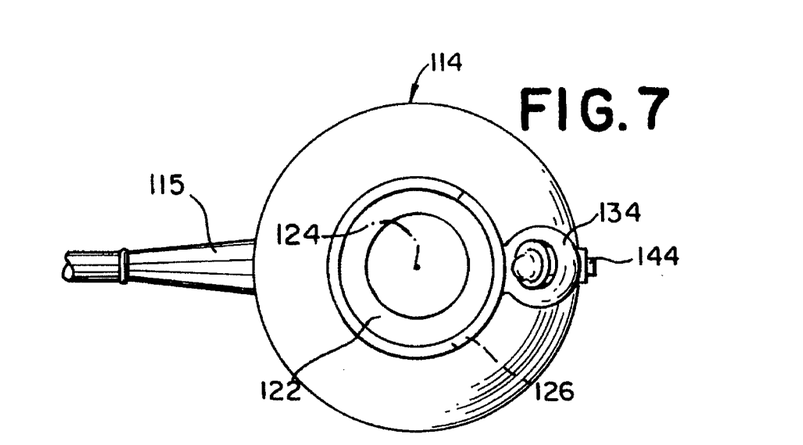
FIG. 7 is a bottom plan view of the device of the probe of FIGS. 5 and 6.

Referring to FIGS. 5–7, a second embodiment centering device 130 of the present invention, which is mounted on the instrument or probe 114 of a preferably portable apparatus for determining Brinell hardness of a specimen by automatic diametric measurement of a Brinell indentation in the specimen. Apart from the below noted changes in probe 114, the instrument is preferably otherwise like the instrument 10 of FIG. 1.

Probe 114 includes a housing indicated generally at 116 containing a photoresponsive subsystem with at least some optics, which probe optics are indicated diagramatically at 118. One or more artificial illumination sources, indicated diagrammatically at 119, are provided on the probe 114. Again, the source(s) 119 can be configured to direct light parallel to a central axis 124 of the probe or at an angle to that axis. One end 120 of the probe is preferably planar to be placed on a planar specimen surface indicated at 12. The housing has an opening 122 at the one probe end 120 which is at least generally aligned and, preferably coaxial with respect to a central axis 124 of the opening and housing and to the optics 118 so as to provide to the photoresponsive subsystem including the probe optics 118, a field of view of the specimen surface 12 through opening 122 when the one end 120 is located against the specimen surface 12. Opening 122 is also sufficiently large so as to provide to the optics 118 a field of view of the specimen surface 12 opposite the one end 120 sufficiently large to fully view and permit the diametric measurement of any Brinell indentation 13 in surface 12 aligned opposite the opening 122.

Centering device 130 preferably comprises an alignment light source 134 separate from the illumination source 119, which generates a beam 140 of visible light as an alignment guide. "Visible light" as used in this application refers to the visible light spectrum of wavelengths between about four and seven thousand angstroms. Light source 134 is preferably located on the exterior of the probe housing 116 so as to not interfere with the field of view of the probe optics 118. A cut-out 126 is preferably provided in a side wall of the housing 116, proximal the one end 120. Source 134 is preferably oriented to direct alignment guide beam 140 through cut-out 126 and through the opening 122 and out of the housing 116. The center of beam 140 might be aligned to intersect the central axis 124 in the plane of the one end 120 where the central axis 124 would normally intersect the planar surface of the specimen 12 against which the one end 120 was placed. The beam 140 produces a visible light illumination intensity level at opening 122 greater than the level produced there by illumination source 119 and sufficiently great to permit an operator to align the probe end with an indentation in a specimen surface using only the light beam 140 to locate the probe opening and guide it to an indentation.

While the probes of known, electro-optical Brinell hardness determining apparatus include an illumination source 119, such source is either infra-red or produces low level visible light. The former obviously produces no level of visible light intensity while the latter produces visible light which is very faint and diffuse to minimize glare and to otherwise enhance illumination of a Brinell indentation for measurement purposes only. Neither type of illumination source has been adequate to enable an operator using such instruments to use the illumination source alone to align the probe end with Brinell indentations.

Preferably, light source 134 is a compact laser generating a very intense beam of visible light 140 having a diameter on the order of only about one millimeter or so. The smaller the diameter of the beam, assuming the beam is still of a sufficiently high illumination intensity, the more quickly and closely the probe central axis 124 and opening 122 can be aligned with the Brinell indentation in the specimen surface 12 by an operator simply observing the probe end 120 on specimen surface. Further fine alignment, if necessary, would be performed through an operator display providing a magnified view of the surface through the probe optics. However, more sophisticated apparatus include the capability of determining Brinell indentation diameters, even when the indentation is off-center and out of exact alignment with the central axis 124 of the probe 114. The present invention can thus be used with such apparatus as the sole means provided for alignment of the probe end 120 with the indentation 13 for measurement purposes and an operator specimen surface display dispensed with entirely. Again, this is particularly valuable with portable units where specimen surfaces must be computer generated for display on a liquid crystal device.

In newly designed instruments, the light source 134 can be incorporated into the design of the probe housing. In the absence of such original incorporation, it may be necessary to mount a light source 134 in some way, such as with a collar 136, which might be designed to replace a similar collar of similar diameter originally provided at the one end of the probe 114. A threaded coupling between the replacement collar 136 and the remainder of the probe 114 is indicated at 138. Collar 136 would replace an original, cylindrical portion of the housing 116 and would contain an opening 122 identical or at least nearly identical in size to the original opening at the one end of the original probe 114.

Not only does cut-out 126 provide a means for passing the light beam 140 from the exterior of the housing 116 through the housing and then through the opening 122, it permits an operator to view the beam's impact on the specimen surface, when the end 120 is placed against the surface, so as to more closely align the probe central axis 124 with the center of a Brinell indentation 13 beneath the one end 120 of the probe.

While a laser light source 134 is preferred, a non-coherent visible light source together with a suitably configured optical system can be provided to generate a beam of bright, non-coherent, visible light passing through the opening 122 at the one end 120 of the probe sufficiently narrow to permit alignment of such beam and the central axis 124 with a Brinell indentation 13. Preferably, such beam, if directed through a cut-out like cut-out 126 and through opening 122, would be sufficiently sharp and narrow to prevent or, at the very least, minimize reflections from the inner and outer walls of the probe housing 116, which might interfere with the operator's view through the cut-out.

It is also believed possible to eliminate separate light source 134 and to provide a visible light illumination source which is operated at high and low illumination intensity levels for initially aligning the probe end with the indentation and then measuring the diameter of the indentation.

Moreover, while direct projection of the beam 140 from the light source 134 through the cut-out 126 and opening 122 is shown, one of ordinary skill will appreciate that the beam 140 could be directed through the opening 122 in other ways. For example, a transparent planar lens might be provided in housing 116 and oriented so as to not interfere with light transmitted from the opposing end of the housing 116 through the opening 122 or reflected back from an indentation 13, and yet oriented to reflect the beam 140 downward through the opening 122. In this way, it might be possible to virtually align at least a portion of the beam passing through the opening 122 coaxially with the central axis 124, as the axis projects from the one end 120 of the probe 114.

Centering device 130 preferably further comprises a switch, indicated diagrammatically at 144, coupled with light source 134 to selectively manually activate and extinguish the alignment light source 134 separately from any operation of the illumination source(s) 119. Alternatively, the alignment light source 134 and the instrument can be configured so that activation of source 134 is controlled by the instrument to synchronize the extinguishing of light source 134 with operation of the illumination source(s) 119 provided when the diameter of the indentation is actually being measured, or vice versa. Where the photoresponsive subsystem is essentially insensitive to the frequency of the alignment beam light, for example, where an infra-red detector is used, it may be possible to operate light source 134 continually. Again, the visible light source(s) 119 may be configured to operate at different intensity levels for alignment and measurement steps and to be switched between those levels, either manually or automatically under control of the system, for example, when a signal is generated to control the taking of a diametric indentation measurement.

While this preferred embodiment of the invention comprises a laser mounted on the probe 114, the alignment light source 134 might alternatively comprise an incandescent bulb, high intensity LED or other conventional visible light generator with a focusing lens, lens train or optical wave guide. Also, one of ordinary skill will appreciate that the laser, incandescent bulb or other light generator might even be located remotely from the probe, for example, in the processor portion of the instrument, and light produced by the generator carried through the cabling 115 to the probe 114 by suitable means, such as a fiber optic wave guide, to be projected from inside the housing 116 through the opening 122. The illuminated end of the fiber optic wave guide in such an embodiment would constitute the alignment light beam source associated with the probe.

Also, one of ordinary skill will appreciate that if a non-coherent light source is used for alignment, the light source might be used simply to generate visible, non-coherent light within the housing 116. The housing interior and/or its opening 122 can be configured to confine the light to a defined beam 140 projecting from the one end 120 through the opening 122, like a flashlight.

The remaining FIGS. 8–11 depict an electro-optical instrument or probe indicated generally at 214, which is an improvement over probe 14 of FIGS. 1–3. Probe 214 would continue to be used with an electronic processor 16 and keyboard 19 or a keypad (not depicted). However, the superior performance of this device may render an optical display in the form of a CRT or liquid crystal screen for generating a reproduction of the specimen surface unnecessary.

Probe 214 preferably includes a generally tubular upper body 216 having a central longitudinal passageway 217, a generally tubular lower body 218 having a central longitudinal passageway indicated in phantom at 219 and coaxial with 217, a frustoconical lower housing member 228, which receives the lower body 218 and is secured to a lower end of the upper body 216, and a cylindrical, upper housing member 229, which is secured with the uppermost end of the upper body 216. Upper body 216 and upper and lower housing members 228 and 229 collectively define a housing of the probe. Probe 214 preferably contains a plurality of internal light sources, which are indicated in the various figures at 223a, 223b, 223c and 223d, preferably each being in the form of a light emitting diode ("LED"). The LED's 223a–223d are preferably mounted in the lower body 218 at orthogonal and symmetric positions around an axis 226. Axis 226 is preferably central to the probe 214, each of the upper and lower bodies 216, 218 and their passageways 217 and 219, respectively, and to the preferred optics, which are to be described.

Lower end 224 of the probe 214 is provided with an opening 225 preferably centered along and symmetric with respect to the central axis 226. Opening 225 is preferably defined by a generally annular alignment member 240, which is secured in a circular recess in the lower end of lower body 218. Annular alignment member 240 further secures a preferably annular light screen 232 between itself and the LED's 223a–223d. The alignment member 240 includes mutually perpendicular arms 243–246 which come together along the central axis 226 and flare at their ends remote from the central axis 226 for strength and to better channel light, as will be explained. Mutually adjoining, preferably radially curved portions of each of the arms 243–246 define a centering structure 248, which protrudes from the remainder of the annular alignment member 240.

Figure 10:
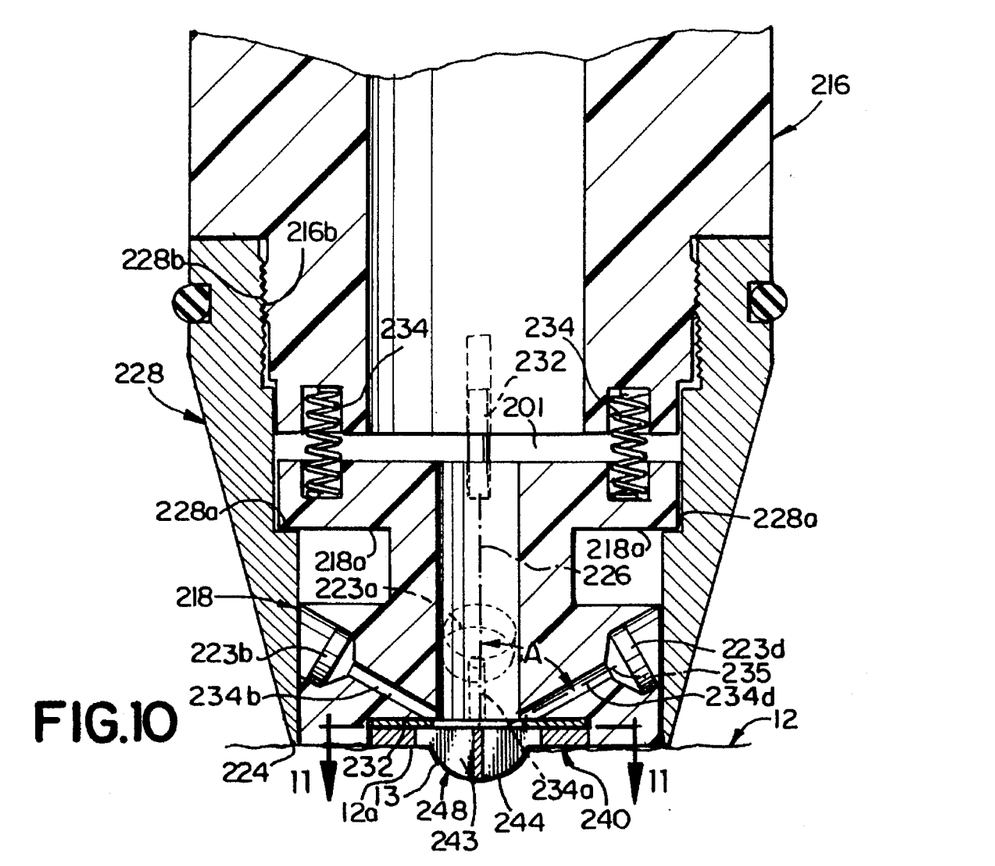
FIG. 10 is an expanded cross-sectional view of the lower working end of the probe of FIGS. 8 and 9.
Figure 11:
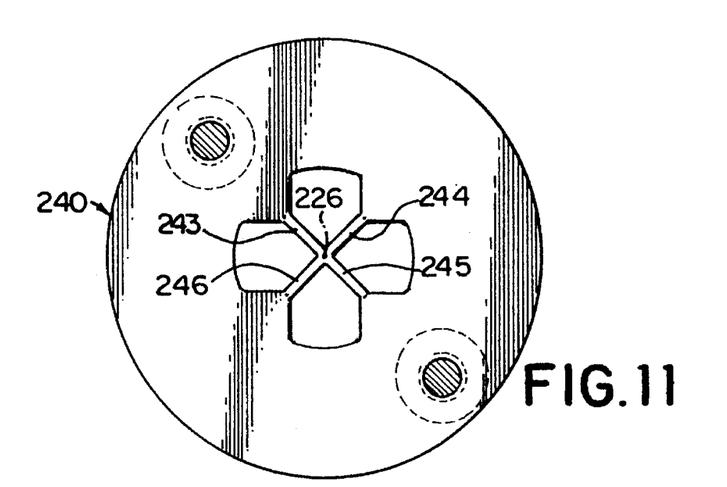
FIG. 11 is an expanded bottom plan view of the probe of FIGS. 8 through 10.

Referring to FIGS. 10 and 11, in particular, each of the LED's 223a–223d is positioned to face and generally bisect a mutually adjoining pair of the arms 243–246. Preferably, each LED 223a–223d is mounted so as to project essentially or at least substantially all of its light output directly against the adjoining pair of the arms 243–246, which it bisects, and to project little if any of its light output directly on the exposed surface of the indentation 13 engaged with the centering structure 248 of the alignment member 240 or on the outer surface 12a of the specimen 12 at least immediately adjoining the indentation 13. To accomplish this result, light from each LED is preferably channeled along one of a set of relatively narrow bores 234a–234d, for example, only about 52 mils in diameter, extending through the lower body 218 and into the central passageway 219. The centerline of each bore 234a–234d is pointed directly at the center of the bisected legs along the central axis 226. Preferably, centerline 235 of bore 234d forms a lesser included angle A with respect to the central axis 226, which is between 45° and 90° and, preferably, is about 60° or more so that light from the LED 223d does not fall directly on the surface of the indentation 13 but must be reflected or at least scattered from the alignment member 240, particularly the directly opposing pair of arms 244, 245 bisected by bore 234d, which direct the light on the surface of indentation 13. Annular light screen 232 is further provided, configured and positioned to prevent light projected by any of the LED's 223a–223d, from falling directly on or being returned from the centering structure arms 243–246 on to any of the specimen surface 12a surrounding indentation 13, particularly anywhere from the edge of the indentation 13 radially outwardly, when the lower end 224 of the probe 214 is positioned abutting the surface 12 with centering structure 248 in the indentation 13.

It has been found that when the foregoing additional precautions are taken, a significantly greater level of contrast can be developed between the surface of the indentation 13 and the immediately surrounding surface 12a of the specimen. The level of contrast achievable by this embodiment with light screen 232 is so high and so uniform completely around the indentation 13 that it permits highly accurate determination of diametric measurement with a single illumination of the indentation 13. In contrast, the prior art probes without alignment members 40 or 240 typically required multiple illuminations from different sides of an indentation and multiple diametric readings, which were averaged, to assure minimally acceptable accuracy of the diametric determinations. This was found necessary because the level of contrast developed by the prior art probes between the indentation and the specimen surface surrounding the indentation were still relatively low as a result of the uniformity of the illumination in and around the indentation. The performance of probe 214 is noticeably improved even over the performance of probe 14. Because of the uniformly high contrast developed by probe 214 all around the edge of the indentation 13 as a result of screen 232, indentation diameters and thus hardnesses have been found to be more accurately determined more readily with probe 214 than with the probe 14 lacking these improvements.

Figure 8:
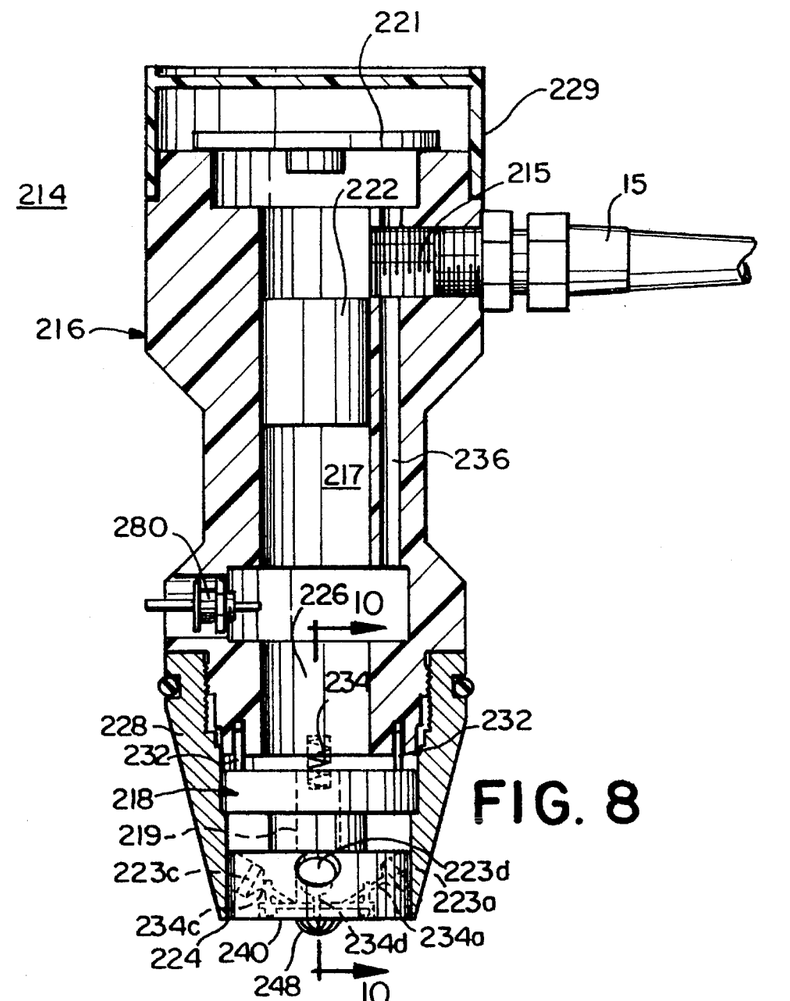
FIG. 8 is a cross-sectional elevational view of an improved probe.
Figure 9:
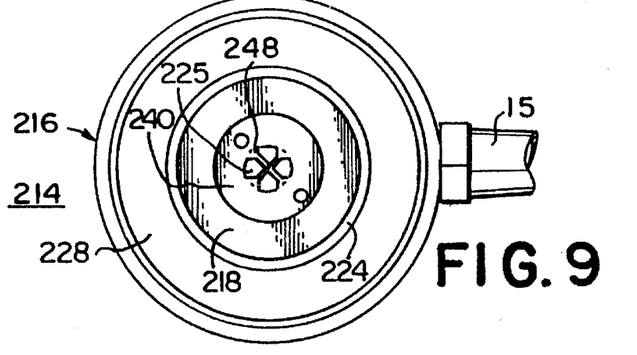
FIG. 9 is a lower plan view of the probe of FIG. 8.

Upper body 216 further preferably mounts the probe optics. Preferably the probe optics include a photoresponsive sensor indicated diagrammatically at 221 and an appropriate lens system indicated diagrammatically at 222. Lens system 222 focuses on the sensor 221, a view of the indentation 13 and the immediately surrounding specimen surface 12a, which is passed by the passageways 217 and 219 of the upper and lower bodies 216 and 218, respectively, the central opening 225 of alignment member 240, and the central opening of annular screen 232.

Preferably a momentary contact switch 280 is provided on the probe 214, preferably supported by the upper body 216, to permit an operator to signal the processor 16 when to activate the LED's 223a–223d and to store the resulting image falling on the sensor 221. Cabling 15, which couples the probe 214 with other components of the apparatus, is preferably received through a radial bore 215. Individual wires (not depicted) are coupled with sensor 221 and switch 280, and passed through a longitudinal bore or groove 236 on the upper body 216 to the LED's 223a–223d on lower body 218.

Preferably lower body 218 is movably mounted with respect to the upper body 216. This is preferably accomplished through the lower housing member 228, which receives and preferably slidably supports the lower body 218. A downward interference stop is provided between a downward facing lip 218a on the lower body 218 and an upward facing inner lip 228a on conical member 228 to retain lower body 218 in lower housing conical member 228. Member 228 has threads 228b which mate with threads 216b of upper body 216. A gap 201 is provided between the upper end of lower body 218 and lower end of upper body 216 to permit lower body 218 to withdraw into conical member 228. Lower body 218 is preferably guided by an inner cylindrical wall of conical member 228 and at least one or preferably a pair of positioning pins 232, which are preferably diametrically positioned on either member 216 or 218, or on each member, and which are slidingly received in appropriately positioned bores in the remaining, opposing member. A pair of coil springs 234, are preferably provided between the upper and lower bodies 216, 218, diametrically positioned with respect to the central axis 226, and orthogonally positioned with respect to the pin(s) 232 so as to bias lower body 218 and the alignment member 240 down and away from the remainder of the probe 214. This ensures that the centering structure 248 of alignment member 240 will project from the lower end 224 of the probe 214 into any indentation 13 aligning with the centering structure 248 as the probe 214 is moved across the specimen surface 12 on the lower ends of lower housing member 228 and the centering structure 248. Elements 218, 228, 240, 232, 234a–234d collectively define a centering device like centering device 30 of the first probe embodiment 14.

The axial movement permitted in the lower body 218 is important in several respects. While the radius of curvature of the arms 243–246 defining centering structure 248 is 2.5 or 5 mm to coincide with the radius of curvature of the indentor tool used to make indentation 13, preferably the centering structure 248 protrudes only about one-sixteenth of an inch from the remainder of annular member 240 and the remainder of the lower end of probe 214. This dimension is much less than the five or ten millimeter diameter of the indentor used to make indentation 13. However, indentations in hard materials are rarely if ever as much as one-sixteenth of an inch (1.6 mm) in depth. Accordingly, centering structure 248 is typically not even fully received in most indentations 13 which will be engaged with the structure 248. Obviously, larger structures 248 can be used if deeper indentations are expected. The indicated construction permits the lower body 218 to withdraw into the lower housing member 228 sufficiently so that the annular flat end of the lower housing member 228, which surrounds the lower body 218 and annular alignment member 240, can abut flushly against the specimen surface 12a. This both fixes the distances between the specimen surface 12a and the lens system 222 and sensor 221, which is typically relatively sensitive to focal length, and prevents ambient light outside the probe 214 from falling on the indentation 13 and, more importantly, the specimen surface 12a immediately surrounding the indentation. The latter helps to assure that the high level of light contract developed by probe 214 between the indentation 13 and surrounding surface 12a is maintained. Opening 225 and the central opening through light screen 232 each may be about 8 mm in diameter.

Commercial components might be used in the probe 214. Lens system 222 might be, for example, a six element, microreader type lens (F 3.5–25 or equivalent), which may be obtained from Universal Kogaku in Oyster Bay, N.Y. The LEDs 223a, 223d may be Seimens Part No. SFH 485P or equivalent. Photoresponsive sensor 221 may be a Texas Instruments Model TC 221 512×512 pixel CCD device, Sony XC77, Pullnix board level camera, or the equivalent. Momentary switch 180 may be an Archer Part No. 275–1571 or equivalent, from the Tandy Corporation.

Use and operation of the probe 214 and related hardness determining system is as follows. The probe 214 is centered over the Brinell impression 13 on the specimen surface 12a by running the end 224 of probe 214 against the surface of the specimen 12 until the centering structure 248 engages and extends into the impression 13. The lower surface of the lower housing member 228 is pressed against the specimen surface 12a to assure direct contact between that end of the member 228 and the surface 12a. The operator then depresses the switch 280, which signals the processor 16 to provide signals illuminating the LED's 223a–223d and to latch and transmit the visible light intensity levels sensed by the individual cells of the photoelectric sensor 221 to the processor 16 for storage and subsequent processing. Each cell of sensor 221 generates data which corresponds to one pixel of the image seen by sensor 221 through central opening 225. Preferably, the processor 16 is programmed to block out or ignore the values from those cells which "read" the individual arms 243–246 of the centering structure 248. Preferably the cells of sensor 221 in rectilinear rows and columns and one positioned with respect to member 240 such that arms 243–246 extend along what are "diagonals" of the cell "rows" and "columns".

Preferably the processor 16 examines the data received from the cells along twenty central columns of the sensor 221, preferably in subarrays, for example 10×20 pixel (cell)

subarrays, from the "top" of the columns to the "bottom" of the columns to identify the two 10×20 subarrays which overlap the upper and lower edges of the impression 13. Preferably processor 16 does this by initially identifying the numbers of cells in the subarray generating intensity values above a first, upper predetermined limit, which are presumed to constitute illuminated areas, and pixel values falling below a second, lower predetermined limit, which are presumed to constitute shadow areas. When a subarray is found having pixels intensities above the first predetermined limit (for example, 180/256) and below the second lower predetermined limit (for example, 80/256), the subarray is more closely examined to identify the indentation boundary. The light intensity levels of adjoining pairs of pixels in each column are examined and those pairs in each column having the greatest transition or change in illumination intensity (light/dark difference) are identified and saved as tentative coordinates of the edge of the indentation 13. The processor 16 then searches for a second subarray of the central columns containing the opposing edge of the indentation and the process is repeated until the coordinates of the lower edge of the impression 13 is similarly identified in a second subarray of the twenty columns of cells.

The processor 16 estimates a diameter of the indentation from the high transition pixel pair coordinates identified from the two subarrays. The processor 16 then identifies an annular sector in each quadrant defined by the arms 243–246. Each sector may be, for example, about 20 pixels wide, centered on the circumference of a circle estimated from the two subarrays of the original twenty columns. Preferably the processor 16 compares the light intensity levels of the pixels within the defined annular sector and identifies those pixels most likely to be seeing an edge. Preferably, the processor uses conventional filtering techniques such as Sobell filtering, to examine each pixel in the defined annular sector by comparing its intensity level with that of its neighboring pixels to assign a weighted value which will identify the pixel as being fully in the indentation (maximum illumination intensities), fully outside the indentation (minimum illumination intensities) or spanning the indentation and, in the latter case, the degree to which the pixel is presumed to span the indentation.

The presumed coordinates of the edge of the indentation are preferably analyzed by appropriate statistical means, such as a best-fit function (e.g. least squares regression), to identify the number of pixels which were identified as spanning the edge and lying within the initially defined distance (±2 pixels) from the estimated circumference location. If a sufficient minimum number of transition locations are identified as lying within that range, the original estimate of diameter is reestimated based upon all of the identified pixel pairs and the hardness of the sample determined in a conventional fashion from the reestimated diameter. The processor 16 can further be programmed to compute and display a confidence level for the determined hardness based upon the actual number of transition locations identified and their locations within the sectors in comparison to the total potential number of transition locations which could have been identified based upon the originally estimated diameter.

Preferably, the processor 16 is programmed to indicate to the operator when an insufficient number of high transition locations have been identified within the standard sector to provide at least a minimally acceptable confidence factor (e.g. 0.8) and to thereafter permit the operator to vary the radial width of the sectors until a minimally acceptable number of adjoining pixel pairs having sufficiently high intensity level differences have been identified and to then provide a best estimate of the diameter of the indentation and of the resulting hardness of the sample. This is most likely to occur where the indentation is misshapen (i.e. non-circular). The process can be accomplished in a variety of ways, including having the processor 16 generate a single estimate of diameter/hardness with a specific confidence factor less than the minimal predetermined confidence factor or a range of diameters/hardnesses believed to fall within a predetermined minimal confidence factor, or both. Alternatively, software can be obtained from a vendor specializing in such matters such as Mnemonic Inc., Mt. Laurel, N.J.

In view of the foregoing, others may attempt to duplicate applicant's success in illuminating essentially only the indentation and none of the adjoining specimen surface. One alternate way to do so would be to use the protruding centering structure 48 as a light source. For example, an optical wave guide could be provided along central axis 226 as a junction for the plurality of individual arms 243–246, or some or all of the arms 243–246 can be formed with or as one or more optical wave guides or like transmitting material. In these versions, the wave guide or like transmitting material would deliver light to the extreme end of the centering structure 48 from which it would issue outwardly into the impression 13 and illuminate the impression 13 from within. Alternatively, optical wave guide(s) and/or lens systems may be substituted for the LED's themselves to project light onto the alignment member 240 from a source within the probe 214 or from somewhere else in the apparatus. All of the foregoing means of illumination are considered to be usable as part of the present invention.

One of ordinary skill will further appreciate a significant benefit of the centering devices of the present invention in simplifying the process of aligning the working end of a Brinell hardness determining instrument with a Brinell impression in a specimen surface, to make the alignment process quicker and at least as accurate if not more accurate and, further, the benefit of eliminating the need to provide or generate a display reproducing a specimen surface for an operator. The indentation illumination provided by alignment members 40 and 240, particularly with light screen 232 or the equivalent, permits accurate hardness determination readings to be taken in 1/30th of a second, the time needed to illuminate an indentation once and save the resulting illumination data. In contrast, prior probes without members 40, 240 or 232 required several consecutive illuminating of an indentation from several different sides to reconstruct a sharp indentation edge profile entirely around an indentation. This required the operator to hold the probe motionless for several seconds. Any movement of the probe could degrade the accuracy of the result or invalidate the measurement, requiring another new measurement cycle of the device. One of ordinary skill will appreciate that it may be desirable to combine centering devices 40 and 240 in a single instrument.

While preferred mechanical and photomechanical centering devices for electro-optically configured and optically configured Brinell hardness determining instruments has been described and variations to the instruments and preferred devices suggested, still other variations thereto are clearly possible and would be known to others of ordinary skill in this art. Accordingly, the invention is not limited to the precise embodiment disclosed but rather is intended to cover any modifications which are within the scope and spirit of the invention, as defined by the appended claims.

We claim:

1. In an electro-optical apparatus for determining hardness of a specimen by diametric measurement of an indentation in a surface of the specimen, the apparatus including a probe and an electronic processor coupled with the probe, the probe including an opening at one end thereof, the probe further including an artificial illumination source located to illuminate a specimen surface through the opening and optics within the probe located to view the specimen surface exposed through the opening as illuminated by the illumination source, an improvement comprising a separate centering device having an alignment guide projecting outwardly from the probe through the opening, the alignment guide entering an indentation when the indentation is at least generally aligned with the opening.

2. The centering device of claim 1 comprising an alignment light source separate from the illumination light source, the alignment light source being mounted on the probe to project a beam of visible light out of the probe through the opening and the alignment light source developing a visible light intensity level at the opening greater than an intensity level of visible light developed at the opening by the illuminating light source, the alignment guide comprising the beam.

3. The centering device of claim 2 wherein the alignment light source comprises a laser.

4. The centering device of claim 2 wherein the alignment light source comprises a non-coherent visible light generator.

5. The centering device of claim 2 further comprising an activation switch coupled with the alignment light source to permit selective activation of the alignment light source.

6. The centering device of claim 1 comprising:

an alignment member having a central axis and two opposing axial sides, the alignment guide comprising a portion of the alignment member protruding generally concentrically with respect to the central axis from one axial side of the alignment member through the opening and forming a centering structure of the alignment member shaped to mate with a generally circular indentation in the specimen surface, a central portion of the alignment member further being configured to freely pass light axially through the alignment member generally around the central axis whereby the field of view of the specimen surface through the opening is at least substantially unblocked.

7. The centering device of claim 6 wherein the alignment member includes at least two arms extending radially with respect to the central axis, at least portions of each of the arms adjoining the central axis protruding generally axially on the one side of the alignment member so as to collectively define at least part of the alignment guide centering structure of the alignment member protruding from the one end of the probe through the aperture generally aligned with the central axis.

8. An improved Brinell hardness-determining apparatus comprising:

an instrument having a housing with an end configured for placement on a specimen surface to be examined and an opening through the end providing a field of view within the instrument of the specimen surface on which the end of the housing is placed;

an alignment member having a central axis and two opposing axial sides, a central portion of the alignment member, being aligned generally with respect to the central axis and protruding from one axial side of the alignment member through the opening aligned to define a centering structure, the centering structure being shaped to mate with a generally circular indentation in the specimen surface, the central portion of the alignment member further being configured to freely pass light axially through the alignment member, generally around the central axis, whereby the field of view of the instrument through the opening is at least substantially unblocked, the central portion of the alignment member further having a generally light distributing surface finish;

at least one light source located proximal the one end of the instrument and positioned to bounce light off the central portion of the alignment member and into the generally circular indentation mated with the alignment member so as to illuminate the circular indentation to a greater degree than the light source illuminates the specimen surface adjoining the indentation.

9. The apparatus of claim 8 further comprising:

a biasing member positioned with respect to the alignment member and the housing to bias the one side of the alignment member and the centering structure axially away from the housing through the opening.

10. The apparatus of claim 9 further comprising:

a coupling securing the alignment member and the bias member with the housing such that the central axis of the alignment member is at least generally coincident with an optical axis of the instrument and the alignment member is supported for movement in the axial direction biased away from the instrument by the bias member.

11. The apparatus of claim 8 wherein the alignment member includes at least two arms extending radially with respect to the central axis, each of the arms protruding generally axially on the one side of the alignment member so as to collectively define at least part of the centering structure of the alignment member protruding from the one end of the apparatus through the opening.

12. The apparatus of claim 11 including at least two additional light sources, each of the three light sources being positioned to reflect a beam of light off an adjoining pair of the arms and into the generally circular indentation mated with the alignment member so as to illuminate the indentation between the adjoining pair of arms to a greater degree than each light source illuminates the specimen surface proximal to the indentation.

13. The device of claim 11 wherein the alignment member has four arms, each arm being perpendicularly positioned with respect to each immediately adjoining arm.

14. The apparatus of claim 13 including at least three additional light sources, each of the four light sources being positioned to reflect a beam of light off an adjoining pair of the arms and into the generally circular indentation mated with the alignment member so as to illuminate the indentation between the adjoining pair of arms to a greater degree than each light source illuminates the specimen surface proximal to the indentation.

15. The apparatus of claim 8 further comprising a screen coupled with the housing and positioned to prevent flight from impinging directly upon the specimen surface proximal to the indentation.

16. The apparatus of claim 15 wherein the screen is positioned between the light source and the indentation and provides a generally circular opening centered on the central axis of the alignment number.

17. The apparatus of claim 16 wherein the light source generates a beam of light reflected from the central portion of the alignment member and wherein a central axis of the beam of light is oriented at a lesser included angle greater than 45° with respect to the central axis, 18. An improved method for hardness determination using diametric measurements of an at least generally circular indentation in a specimen surface comprising the steps of:

illuminating the indentation simultaneously at least essentially entirely around a circumferential edge of the indentation to a greater degree than the specimen surface is illuminated immediately adjoining the circumferential edge of the indentation and thereby establish a contrast between brighter portions of the indentation immediately adjoining a circumferential edge of the indentation and darker portions of the specimen surface immediately adjoining the circumferential edge at the same time at least essentially entirely around the indentation; and sensing illumination intensity from the indentation and the specimen surface immediately adjoining the circumferential edge of the indentation at least essentially entirely around the indentation from directly opposite the indentation during the illuminating step.

19. An improvement for hardness determination using diametric measurements of an at least generally circular indentation in a specimen surface comprising the step of: illuminating the indentation to a greater degree than the specimen surface is illuminated proximal to the indentation and thereby establish a contrast between brighter portions of the indentation and darker portions of the specimen's surface immediately adjoining the brighter portions of the indentation, simultaneously at least essentially entirely around the indentation.

20. A method of material hardness determination comprising the steps of:

illuminating at least essentially all of an indentation in a material specimen surface at the same time for a fraction of a second;

sensing at one time illumination intensities from essentially all surfaces of the indentation once during the illuminating step while at least essentially all of the indentation is being illuminated; and using only the once sensed illumination intensities to determine hardness of the material specimen.

21. An improved method for hardness determination using diametric measurements of an at least generally circular indentation in a specimen surface comprising the steps of:

illuminating the indentation to a greater degree than the specimen surface is illuminated immediately adjoining the circumferential edge of the indentation and thereby establish a contrast between brighter portions of the indentation immediately adjoining a circumferential edge of the indentation and darker portions of the specimen surface immediately adjoining the circumferential edge at least essentially entirely around the indentation by inserting a member into the indentation and reflecting illumination off the member into the indentation; and sensing illumination intensity from the indentation and the specimen surface immediately adjoining the circumferential edge of the indentation through the member at least essentially entirely around the indentation from directly opposite the indentation during the illuminating step.

* * * * *